| United States Patent [19] | [11] | 4,254,062 |
|---|---|---|
| Wambach et al. | [45] | Mar. 3, 1981 |

[54] SEPARATION PROCESS

[75] Inventors: Raimund Wambach, Leverkusen; Sigurd Hartung, Cologne; Gerhard Reiss; Lothar Puppe, both of Leverkusen, all of Fed. Rep. of Germany

[73] Assignee: Bayer Aktiengesellschaft, Leverkusen, Fed. Rep. of Germany

[21] Appl. No.: 2,501

[22] Filed: Jan. 10, 1979

[30] Foreign Application Priority Data

Feb. 1, 1978 [DE] Fed. Rep. of Germany ....... 2804203

[51] Int. Cl.³ .............................................. C07C 25/02
[52] U.S. Cl. .................................................... 570/211
[58] Field of Search ................................... 260/650 R

[56] References Cited

U.S. PATENT DOCUMENTS

| 1,946,040 | 2/1934 | Stoesser et al. | 260/650 |
|---|---|---|---|
| 2,882,244 | 4/1959 | Milton | 423/328 |
| 2,958,708 | 11/1960 | Fleck et al. | 260/650 R |
| 3,130,007 | 4/1964 | Breck | 423/328 |

*Primary Examiner*—Curtis R. Davis
*Attorney, Agent, or Firm*—Sprung, Felfe, Horn, Lynch & Kramer

[57] ABSTRACT

A process for the separation of isomeric dichlorotoluenes is described wherein an isomeric mixture of dichlorotoluenes is passed over a zeolite of the X or Y type, non-adsorbed dichlorotoluene is separated off and the adsorbed dichlorotoluene is eluted from the zeolite by contacting the same with an eluant.

13 Claims, No Drawings

SEPARATION PROCESS

The invention relates to a process for the separation of isomeric dichlorotoluenes with the aid of zeolites.

The separation of an isomer mixture of ortho- and para-chlorotoluene and ortho- and meta-dichlorobenzene with the aid of a calcium zeolite of the X type is known from U.S. Pat. No. 2,958,708. The ortho-isomer is somewhat more strongly adsorbed on the zeolite than the para-isomer, but the separation effect is low. In the case of the p/m-di-chlorobenzene mixture, the meta-isomer is most strongly adsorbed (U.S. Pat. No. 2,958,708, Example 1).

A process has been found for the separation of isomeric dichlorotoluenes, which is characterised in that the mixture of isomeric dichlorotoluenes is treated with a zeolite of the X or Y type, the non-adsorbed dichlorotoluenes are then separated off in a manner which is in itself known and the adsorbed dichlorotoluene is subsequently eluted with an auxiliary which has a displacement action and is adsorbed to a small extent on the zeolite.

Zeolites of the X and Y type for the process according to the invention are crystalline aluminosilicates which have a faujasite structure and can be represented by the formula below:

$$(1.0 \pm 0.2)M_{2/n}O: Al_2O_3: w\ SiO_2$$

wherein
M is a cation with a valency of n and
w is a number from 2 to 6.

In general, synthetic faujasite with values for w of 2 to 3 are called zeolite X, and those with values for w of 3 to 6 are called zeolite Y.

It is known that zeolites of the X and Y type can be employed in certain adsorptive separation processes. The preparation of these zeolites is described in U.S. Pat. Nos. 2,882,244 and 3,120,007. In the case of zeolites of the X and Y type in the form in which they are originally prepared, the cation M usually consists predominantly of sodium.

Zeolites in which all or some of the sodium as the cation M is replaced by monovalent or divalent cations, for example potassium, barium and strontium, are preferably employed for the process according to the invention. It is, of course, possible for one or more different cations to be the cation M in a zeolite. Such zeolites can be prepared by methods which are generally known in the field of crystalline aluminosilicates.

The proportions of the individual cations M can vary within wide limits; thus, for example, the 2 molar equivalents of the cation M can consist of at least 20 parts, preferably 50 to 100 parts, of potassium, of at least 20 parts, preferably 50 to 100 parts, of barium or at least 20 parts, preferably 80 to 100 parts, of calcium. A zeolite can, of course, also contain different cations M; thus, a zeolite which is preferred for the process according to the invention contains at least 50 parts of barium and 1 to 50 parts of potassium; a zeolite with 70 to 90 parts of barium and 1 to 10 parts of potassium is particularly preferred.

Zeolites of the X and Y types with the molar compositions which follow can be employed, for example, in the process according to the invention:

0.95 Na$_2$O.2.5 SiO$_2$.Al$_2$O$_3$
0.05 Na$_2$O.0.91 CaO.2.5 SiO$_2$.Al$_2$O$_3$
0.38 Na$_2$O0.55 K$_2$O.2.5 SiO$_2$.Al$_2$O$_3$
0.12 Na$_2$O.0.8 K$_2$O.2.5 SiO$_2$.Al$_2$O$_3$
0.15 Na$_2$O.0.72 BaO.0.06 K$_2$O.2.5 SiO$_2$.Al$_2$O$_3$
0.63 BaO.0.041 K$_2$O.2.5 SiO$_2$.Al$_2$O$_3$
0.16 Na$_2$O.0.73 BaO.2.5 SiO$_2$.Al$_2$O$_3$

The chlorotoluene mixtures which can be separated or concentrated by the process according to the invention can contain isomeric dichlorotoluenes in various proportions.

The preparation of such dichlorotoluene mixtures is known and can be effected, for example, by chlorinating toluene or monochlorotoluene in the presence of sulphur compounds (U.S. Pat. No. 1,946,040).

In virtually all cases of chlorination of toluene, only in mixture of 5 dichlorotoluenes, namely 2,3-, 2,4-, 2,5-, 2,6- and 3,4-dichlorotoluene, is formed.

The dichlorotoluene isomer mixture which is obtained by chlorinating toluene and separating off toluene, chlorotoluenes and trichlorotoluenes in a simple manner by distillation can contain the isomers in the following proportions: 20 to 35% of 2,4-dichlorotoluene, 25 to 55% of 2,5-dichlorotoluene, 5 to 25% of 2,6-dichlorotoluene, 8 to 12% of 2,3-dichlorotoluene and 5 to 12% of 3,4-dichlorotoluene.

If, for example, o-chlorotoluene is used as the starting material for the chlorination, a mixture having the composition which follows is obtained if o-chlorotoluene trichlorotoluenes are first separated off in a simple distillation: 10 to 25% of 2,4 dichlorotoluene, 30 to 70% of 2,5-dichlorotoluene, 5 to 30% of 2,6-dichlorotoluene and 5 to 20% of 2,3-dichlorotoluene.

In the preparation of the dichlorotoluenes, the composition of the isomer mixture can be varied only to a small extent by catalysts or by changing the temperature (U.S. Pat. No. 1,946,040).

It is indeed possible to divide the isomer mixture into 2 fractions by distillation, one fraction containing the isomers which boil at about 201° C. (namely 2,4-, 2,5- and 2,6-dichlorotoluene) and the other containing those which boil at about 208°-209° C. (namely 2,3- and 3,4-dichlorotoluene), but it is not possible to isolate pure isomers from the two fractions solely by distillative means in an economic manner unless, as is the case, for example, in the reaction mixture obtained from o-chlorotoluene, only 2,3-dichlorotoluene is present in addition to 2,4-, 2,5- and 2,6-dichlorotoluene. In this case, 2,3-dichlorotoluene is advantageously isolated by distillative means. Or in the case of the chlorination of p-chlorotoluene, in which a mixture of 2,4- and 3,4-dichlorotoluene (in addition to unreacted p-chlorotoluene and trichlorotoluenes) which can easily be separated by distillative means is thus obtained.

During further separation of the dichlorotoluene isomers by fractional crystallization, however, considerable difficulties are encountered because of the numerous eutectic mixtures.

It is known, however, that separations or concentrations by an adsorption method are more expensive the more components there are present. For the process according to the invention, it is therefore advantageous to separate the isomer mixture to as great an extent as possible, before the separation by adsorption, by distillation or fractional crystallisation.

The separation according to the invention can be carried out in the form of a liquid phase adsorption/desorption process or a gas phase adsorption/desorption process, a temperature range of from 100°–350° C., preferably 150°–300° C., being chosen in the liquid phase and a temperature range of from 100° to 350° C., preferably 200°–300° C. being chosen in the gas phase. The pressure ranges from 1–30 bar.

The throughput depends on the geometric dimensions of the adsorption apparatus and can easily be optimised.

In preferred embodiments of the process according to the invention, 2,6-dichlorotoluene is adsorbed on the sodium or calcium form of the zeolite X or Y, in preference to the isomeric 2,4-dichlorotoluene and 2,5-dichlorotoluene. Barium-containing zeolites X or Y or mixed calcium and barium forms preferentially adsorb 2,4-dichlorotoluene.

The high selectivity for 2,6-dichlorotoluene, in preference to 2,4- and 2,5-dichlorotoluene, of the calcium-exchanged zeolite X or Y is particularly advantageous. Good separation of the 2,6-isomers from the mixture is thereby possible.

Furthermore, surprisingly, not only can 2,6-dichlorotoluene be separated off from the dichlorotoluene isomer mixture, but one can also isolate both 2,4-dichlorotoluene and 2,5-dichltoluene from the mixture.

If the calcium form of the zeolite X or Y is employed for the adsorption, at the start of the liquid phase separation process it exhibits a preferred selectivity for the 2,6-dichlorotoluene isomers, which, during the desorption step after concentration of the 2,6-dichlorotoluene, is converted into an increased selectivity for 2,5-dichlorotoluene, by which means it is possible to concentrate first the 2,6-dichlorotoluene and then the 2,5-dichlorotoluene in one adsorption stage.

This concentration of the 2,6-dichlorotoluene isomer is also possible using the potassium-containing zeolite X or Y.

Concentration of 2,4-dichlorotoluene from the dichlorotoluene mixture is preferably effected in the vapour phase on a mixed barium/potassium form of the zeolite X or Y in the desorbate, or on the sodium/calcium form in the raffinate.

The process according to the invention for the separation of the isomeric dichlorotoluenes can be carried out in apparatus customary for continuous separation by adsorption (Hydrocarbon Processing, November 1970, pages 151 to 155).

In the case of a discontinuous procedure, it is possible, for example, to use a customary adsorption column with a height of 2 to 10 meters. The adsorption column is then filled with a zeolite having a particle size of 0.1 to 2 mm, preferably 0.2 to 1 mm. The zeolite is then charged with the gaseous or liquid isomer mixture and the non-adsorbed dichlorotoluenes are separated off.

After the separation, the adsorbed isomer is eluted with the aid of an auxiliary having a diluting or eluting action. Such auxiliaries can be used, for example, hydrogen, nitrogen, alkanes, such as methane, ethane, propane and decalin, aromatics, such as benzene and toluene, and polar compounds, such as water and ammonia. Preferred auxiliaries are decalin, benzene and toluene.

One can, surprisingly, separate isomeric dichlorotoluene mixtures using the zeolites employed according to the invention. This was not to be expected, since the individual isomers do not differ considerably in their geometric molecular diameters and only exhibit very slight differences in their dipole moments.

The separation of the six isomeric dichlorotoluenes is a particularly difficult problem, since the boiling points and melting points are very close together. Furthermore, individual isomers form azeotropic and eutectic mixtures. It was therefore hitherto virtually impossible to isolate all the isomers from the isomer mixture.

Dichlorotoluenes can be used as intermediate products for dyestuffs products for plant protection, disinfectants, preservatives and pharmaceuticals (Ullmann's Enzyklopädie der techn. Chemie (Ullmann's Encyclopaedia of Industrial Chemistry), 1975, volume 9, page 515)

EXAMPLES

A granular zeolite X with a particle size of 0.4 to 1 mm is used in the Examples.

The zeolites are modified by replacing some of the Na ions by Ca, Ba or K ions and a mixture of Ba/K ions (Table 1).

The adsorption column had a length of 5 m and a volume of 1 liter. The adsorption and desorption pressure was always 1 bar (absolute).

EXAMPLES 1 TO 7

The breakthrough curve of the various dichlorotoluenes during adsorption in the gas phase is determined in Examples 1 to 7 (Table 2). The adsorption of particular dichlorotoluenes can be obtained therefrom.

Before the measurement, the zeolites were flushed with dry nitrogen at 360° C. for 8 hours.

The adsorption temperature was 260° C. and the throughput was 0.25 dm$^3$ of dichlorotoluene/hour/dm$^3$ of zeolite.

TABLE 1

Specification of the exchange forms of zeolite X used
Molar composition

Sample A  0.95 $Na_2O.2.5\ SiO_2.Al_2O_3$
Sample B  0.05 $Na_2O.0.91\ CaO.2.5\ SiO_2.Al_2O_3$
Sample C  0.38 $Na_2O.0.55\ K_2O.2.5\ SiO_2.Al_2O_3$
Sample D  0.12 $Na_2O.0.8\ K_2O.2.5\ SiO_2.Al_2O_3$
Sample E  0.15 $Na_2O.0.72\ BaO.0.06\ K_2O.2.5\ SiO_2.Al_2O_3$
Sample F  0.63 $BaO.0.041\ K_2O.2.5\ SiO_2.Al_2O_3$
Sample G  0.16 $Na_2O.0.73\ BaO.2.5\ SiO_2.Al_2O_3$

TABLE 2

Adsorption in the vapour phase, breakthrough examples

The starting product of Example Nos. 5, 6 and 7 was obtained by first removing 2,3-dichlorotoluene and 3,4-dichlorotoluene from the dichlorotoluene isomer mixture by distillation and concentrating the 2,6-dichlorotoluene isomers, also with the aid of distillation. In the case of Example 4, the 2,3-dichlorotoluene and 3,4-dichlorotoluene were removed from the isomer mixture by distillation.

| Example No. | Sample | Dichlorotoluene composition % by volume | | | | Concentration in % at the outlet of the adsorber at the start of the breakthrough | | | |
|---|---|---|---|---|---|---|---|---|---|
| | | 2,6 | 2,4 | 2,5 | 2,3 + 3,4 | 2,6 | 2,4 | 2,5 | 2,3 + 3,4 |
| 1 | A | 30.0 | 22.8 | 35.4 | 11.8 | 24.0 | 29.0 | 47.0 | 0 |

TABLE 2-continued

Adsorption in the vapour phase, breakthrough examples

The starting product of Example Nos. 5, 6 and 7 was obtained by first removing 2,3-dichlorotoluene and 3,4-dichlorotoluene from the dichlorotoluene isomer mixture by distillation and concentrating the 2,6-dichlorotoluene isomers, also with the aid of distillation. In the case of Example 4, the 2,3-dichlorotoluene and 3,4-dichlorotoluene were removed from the isomer mixture by distillation.

| Example No. | Sample | Dichlorotoluene composition % by volume | | | | Concentration in % at the outlet of the adsorber at the start of the breakthrough | | | |
|---|---|---|---|---|---|---|---|---|---|
| | | 2,6 | 2,4 | 2,5 | 2,3 + 3,4 | 2,6 | 2,4 | 2,5 | 2,3 + 3,4 |
| 2 | B | 30.0 | 22.8 | 35.4 | 11.8 | 18.0 | 40.0 | 42.0 | 0 |
| 3 | D | 30.0 | 22.8 | 35.4 | 11.8 | 44.0 | 11.0 | 45.0 | 0 |
| 4 | B | 34.4 | 22.8 | 42.6 | — | 20.0 | 37.0 | 43.0 | — |
| 5 | A | 80.0 | 20.0 | 0.5 | — | 61.5 | 38.0 | 0.5 | — |
| 6 | E | 80.0 | 20.0 | 0.5 | — | 90.4 | 9.0 | 0.5 | — |
| 7 | F | 80.0 | 20.0 | 0.5 | — | 89.4 | 10.0 | 0.5 | — |

EXAMPLE 8 TO 14

The adsorption and desorption properties of the dichlorotoluenes on the zeolite samples are determined in a so-called liquid phase experiment.

For this determination, the zeolite sample is regenerated with dry nitrogen at 360° C. for 8 hours before starting the experiment. The temperature for the experiment is 180° C. in all cases. Before the adsorption, the zeolite is charged with 400 ml of decalin/dm³ of zeolite, 40 ml of dichlorotoluene mixture/dm³ of zeolite are then metered into the zeolite bed and thereafter the dichlorotoluene is desorbed again with decalin. All the streams flow in the same direction and the throughput is 330 ml/hour/dm³ of zeolite in all cases.

The desorbate leaving the column is analysed and the so-called selectivity factor S is obtained:

The selectivity for 2,6-dichlorotoluene, for example, in preference to 2,4- and 2,5-dichlorotoluene is obtained from the equation:

$$S_{2,6} = \frac{\text{Concentration in the desorbate } \frac{2,6}{2,4 + 2,5}}{\text{Concentration applied } \frac{2,6}{2,4 + 2,5}}$$

The results are summarised in Table 3 which follows.

TABLE 3

Adsorption and desorption properties of dichlorotoluenes on zeolites, adsorption and desorption in the liquid phase Before the treatment with zeolites, the 2,3- and 3,4-dichlorotoluene isomers were removed from all the starting isomer mixtures by distillation.

| Example No. | Zeolite | Composition of the product applied, % | | | Selectivity | | | Amount of decalin used, ml/kg of zeolite | % of dichlorotoluene in the desorbate | | |
|---|---|---|---|---|---|---|---|---|---|---|---|
| | | 2,6 | 2,4 | 2,5 | 2,6 | 2,4 | 2,5 | | 2,6 | 2,4 | 2,5 |
| 8 | Sample B | 34.1 | 23.7 | 41.2 | 3.97 | 0.61 | 0.27 | 1,230 | 4.2 | 1 | 1 |
| | | | | | 4.85 | 0.8 | 0.12 | 1,380 | 14.6 | 4.1 | 1.6 |
| | | | | | 0.96 | 0.89 | 1.13 | 1,540 | 5.4 | 3.5 | 7.1 |
| | | | | | 0.91 | 0.77 | 1.3 | 1,720 | 3 | 1.8 | 4.4 |
| 9 | Sample C | 34.1 | 23.7 | 41.2 | 1.04 | 0.91 | 1 | 1,500 | 1.6 | 1 | 1.9 |
| | | | | | 0.9 | 0.84 | 1.25 | 1,700 | 5.6 | 3.6 | 8.1 |
| | | | | | 1.58 | 0.68 | 0.92 | 2,000 | 3.6 | 1.4 | 2.9 |
| 10 | Sample C | 79.5 | 20 | 0.5 | 1 | 1 | 1 | — | 79.5 | 20 | 0.5 |
| 11 | Sample E | 34.1 | 23.7 | 41.2 | 1.82 | 0.7 | 0.7 | 1,450 | 21.5 | 7.8 | 14.5 |
| | | | | | 1.37 | 0.95 | 0.76 | 1,600 | 10.6 | 5.8 | 8.8 |
| | | | | | 1.76 | 0.77 | 0.7 | 1,750 | 4.9 | 2.0 | 3.4 |
| 12 | Sample F | 79.5 | 20 | 0.5 | 1 | 1 | 1 | — | 79.5 | 20 | 0.5 |
| 13 | Sample F | 34.1 | 23.7 | 41.2 | 0.91 | 0.98 | 1.1 | 2,250 | 9 | 6.5 | 12.2 |
| | | | | | 0.93 | 1.04 | 1.03 | 2,350 | 10.6 | 7.9 | 13.6 |
| | | | | | 1.33 | 1 | 0.75 | 2,450 | 8.3 | 4.8 | 7 |
| | | | | | 1.49 | 1.04 | 0.63 | 2,600 | 3.4 | 1.9 | 2.4 |
| 14 | Sample G | 79.5 | 20 | 0.5 | 0.97 | 1.06 | — | 1,750 | 11 | 3 | 0 |
| | | | | | 1.25 | 0.825 | — | 2,100 | 6.6 | 1.4 | 0 |
| | | | | | 1.54 | 0.66 | — | 2,500 | 3.5 | 0.6 | 0 |
| | | | | | 1.40 | 0.417 | — | 3,000 | 2.6 | 0.3 | 0.2 |

What is claimed is:

1. A process for the separation of isomeric dichlorotoluenes which comprises passing a mixture of isomeric dichlorotoluenes over a zeolite of the X or Y type having a composition, expresses in terms of mol ratio or oxides, as follows:

$$(1.0 \pm 0.2) \, M_{2/n}O: Al_2O_3: w \, SiO_2$$

wherein

M is a cation of valency n and w is a number from 2 to 6.

separated off non-adsorbed dichlorotoluene and thereafter eluting adsorbed toluene from said zeolite by contacting the so adsorped zeolite with an eluant, the adsorption and elution being carried in the liquid phase or in the gas phase at a temperature of 100° to 350° C.

2. A process according to claim 1 wherein M comprises barium.

3. A process according to claim 1 wherein M comprises strontium.

4. A process according to claim 1 wherein the mixture of isomeric dichlorotoluenes or chlorine mixtures containing dichlorotoluene are partially separated into individual isomers or the isomers are concentrated, by distillation or fractional distillation for treatment with the zeolite.

5. A process according to claim 1 wherein the adsorption and desorption are carried out at 150° to 300° C. in the liquid phase.

6. A process according to claim 1 wherein the adsorption and desorption are carried out at 200° to 300° C. in the gas phase.

7. A process according to claim 5 wherein the adsorption and desorption are carried out after treatment of the zeolite with a solvent.

8. A process according to claim 6 wherein the adsorption and desorption are carried out after prior treatment of the zeolite with a solvent.

9. A process according to claim 1 wherein an isomer mixture of 2,3-, 2,4-, 2,5- and 2,6-dichlorotoluene is treated with the zeolite of the X or Y type in the sodium form and 2,3-dichlorotoluene is separated off by elution from the zeolite.

10. A process according to claim 1 wherein an isomer mixture of 2,4-, 2,5- and 2,6-dichlorotoluene is treated with a zeolite of the X or Y type which contains 80 to 100 mol percent of calcium oxide and up to 20 mol percent of sodium oxide and 2,6-dichlorotoluene is separated off by elution from the zeolite.

11. A process according to claim 1 wherein an isomer mixture of 2,4-, 2,5- and 2,6-dichlorotoluene is treated with a zeolite of the X or Y type which contains 50 to 100 mol percent of potassium oxide and up to 50 mol percent of sodium oxide and 2,4-dichlorotoluene is separated off by elution from the zeolite.

12. A process according to claim 1 wherein an isomer mixture of 2,4-, 2,5- and 2,6-dichlorotoluene is treated with a zeolite of the X or Y type which contains 50 to 100 mol percent of barium oxide and up to 50 mol percent of sodium oxide and 2,5-dichlorotoluene is separated off by elution from the zeolite.

13. A process according to claim 1 wherein an isomer mixture of 2,6-, 2,4- and 2,5-dichlorotoluene is treated with a zeolite of the X or Y type which contains 1 to 10 mol percent of potassium oxide and 70 to 90 mol percent of barium oxide and the 2,5-dichlorotoluene is separated off by elution from the zeolite.

* * * * *